United States Patent
Gruenbacher et al.

(10) Patent No.: US 9,696,702 B2
(45) Date of Patent: Jul. 4, 2017

(54) SYSTEMS AND METHODS FOR WIRELESS CONTROL AND MANAGEMENT

(71) Applicant: The Procter & Gamble Company, Cincinnati, OH (US)

(72) Inventors: Dana Paul Gruenbacher, Fairfield, OH (US); Erik John Hasenoehrl, Loveland, OH (US); Faiz Feisal Sherman, Mason, OH (US); William Paul Mahoney, III, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 21 days.

(21) Appl. No.: 14/560,300

(22) Filed: Dec. 4, 2014

(65) Prior Publication Data

US 2015/0088273 A1    Mar. 26, 2015

Related U.S. Application Data (63) Continuation of application No. 13/633,895, filed on Oct. 3, 2012, now abandoned.

(Continued)

(51) Int. Cl.
G05B 23/02    (2006.01)
G05B 15/02    (2006.01)
(Continued)

(52) U.S. Cl.
CPC ............. *G05B 15/02* (2013.01); *A61L 9/035* (2013.01); *A61L 9/037* (2013.01); *A61L 9/12* (2013.01);
(Continued)

(58) Field of Classification Search
CPC . F21L 2/00; H04N 5/225; G05B 15/02; F24F 11/0009; H04W 4/005; G05F 1/66;
(Continued)

(56) References Cited

U.S. PATENT DOCUMENTS 5,276,630 A    1/1994  Baldwin et al.
5,899,367 A    5/1999  Strength et al.
(Continued)

FOREIGN PATENT DOCUMENTS

EP    2 362 714 A1    8/2011
WO    WO 03/017542 A1    2/2003
(Continued)

OTHER PUBLICATIONS

International Search Report; International Application No. PCT/US2013/050822; date of mailing Dec. 17, 2013; 21 pages.
(Continued)

*Primary Examiner* — Hai Phan
*Assistant Examiner* — Zhen Y Wu
(74) *Attorney, Agent, or Firm* — David K Mattheis (57) ABSTRACT

Included are embodiments for wireless control and management. Some embodiments include receiving a first signal regarding a device condition of a service device in an environment, determining a condition type of the device condition, and sending a first request for to correct the device condition, based on the condition type. Some embodiments also include receiving a second signal indicating whether the device condition was corrected.

6 Claims, 8 Drawing Sheets

Related U.S. Application Data (60) Provisional application No. 61/542,312, filed on Oct. 3, 2011.

(51) Int. Cl.

| | | |
|---|---|---|
| *A61L 9/03* | (2006.01) | |
| *A61L 9/12* | (2006.01) | |
| *A61L 9/14* | (2006.01) | |
| *F24F 11/00* | (2006.01) | |
| *G05F 1/66* | (2006.01) | |
| *H04W 4/00* | (2009.01) | |
| *H05B 37/02* | (2006.01) | |

(52) U.S. Cl.
CPC .............. *A61L 9/125* (2013.01); *A61L 9/127* (2013.01); *A61L 9/14* (2013.01); *F24F 11/0009* (2013.01); *G05F 1/66* (2013.01); *H04W 4/005* (2013.01); *H05B 37/0272* (2013.01); *A61L 2209/11* (2013.01); *A61L 2209/111* (2013.01); *A61L 2209/133* (2013.01); *A61L 2209/14* (2013.01); *Y02B 60/50* (2013.01)

(58) Field of Classification Search
CPC ....... H05B 37/0272; A61L 9/035; A61L 9/12; A61L 9/125; A61L 9/127; A61L 9/14; A61L 2209/11; A61L 2209/111; A61L 209/133; A61L 2209/14
USPC ........................................................ 340/3.44
See application file for complete search history.

(56) References Cited

U.S. PATENT DOCUMENTS

| | | | |
|---|---|---|---|
| 7,184,407 | B1 | 2/2007 | Myles et al. |
| 7,324,824 | B2 | 1/2008 | Smith et al. |
| 7,772,986 | B2 | 8/2010 | Olson et al. |
| 8,063,750 | B2 | 11/2011 | Knibbe |
| 8,615,526 | B2 | 12/2013 | Sinha et al. |
| 2002/0178292 | A1 | 11/2002 | Mushkin et al. |
| 2003/0050737 | A1 | 3/2003 | Osann, Jr. |
| 2005/0007249 | A1 | 1/2005 | Eryurek et al. |
| 2005/0094610 | A1 | 5/2005 | de Clerq et al. |
| 2005/0159823 | A1* | 7/2005 | Hayes .............. G05B 15/02 700/19 |
| 2006/0010388 | A1* | 1/2006 | Imhof ............... G05B 15/02 715/734 |
| 2006/0059545 | A1 | 3/2006 | Stanforth |
| 2007/0090960 | A1* | 4/2007 | Miki ..................... H05B 37/02 340/641 |
| 2007/0244572 | A1* | 10/2007 | Farr .................... G05B 15/02 700/12 |
| 2007/0283005 | A1 | 12/2007 | Beliles et al. |
| 2008/0069008 | A1 | 3/2008 | Park et al. |
| 2008/0159494 | A1 | 7/2008 | Quinlan et al. |
| 2008/0218334 | A1 | 9/2008 | Pitchers et al. |
| 2008/0222431 | A1 | 9/2008 | Paniagua et al. |
| 2008/0231111 | A1 | 9/2008 | Hazani et al. |
| 2008/0256445 | A1* | 10/2008 | Olch ................... G06F 19/3418 715/700 |
| 2008/0265799 | A1 | 10/2008 | Sibert |
| 2008/0303707 | A1 | 12/2008 | Larsen et al. |
| 2009/0002981 | A1* | 1/2009 | Knibbe .................. G01S 5/14 362/233 |
| 2009/0250595 | A1* | 10/2009 | Kalitsis .............. G01N 21/3563 250/208.2 |
| 2009/0265488 | A1 | 10/2009 | Birger |
| 2009/0273433 | A1* | 11/2009 | Rigatti ............... H05B 37/0254 340/3.5 |
| 2009/0285227 | A1* | 11/2009 | De Groote .............. H04L 45/00 370/401 |
| 2010/0082485 | A1 | 4/2010 | Lin et al. |
| 2010/0143186 | A1 | 6/2010 | Belmonte et al. |
| 2010/0232354 | A1 | 9/2010 | Patil et al. |
| 2010/0238935 | A1 | 9/2010 | Sendrowicz |
| 2010/0244708 | A1* | 9/2010 | Cheung .............. H05B 37/0218 315/158 |
| 2011/0059752 | A1 | 3/2011 | Garin et al. |
| 2011/0068922 | A1 | 3/2011 | Ross |
| 2011/0120216 | A1* | 5/2011 | Sugimoto ................ F01P 7/164 73/114.68 |
| 2011/0211110 | A1* | 9/2011 | Doublet .................. H04N 7/188 348/370 |
| 2011/0251807 | A1 | 10/2011 | Rada et al. |
| 2011/0260624 | A1* | 10/2011 | Bigge .................... H05B 37/02 315/119 |
| 2011/0299854 | A1 | 12/2011 | Jonsson et al. |
| 2012/0039310 | A1 | 2/2012 | Dahl et al. |
| 2012/0057755 | A1* | 3/2012 | Berkvens .............. H05B 37/029 382/103 |
| 2012/0086360 | A1* | 4/2012 | Weng .................. H05B 41/3922 315/307 |
| 2012/0221720 | A1 | 8/2012 | Trevino et al. |
| 2012/0253527 | A1* | 10/2012 | Hietala .................. G05B 17/02 700/278 |
| 2012/0313535 | A1* | 12/2012 | Bedell ................ H05B 37/0227 315/158 |
| 2013/0006401 | A1* | 1/2013 | Shan ........................ A01G 1/00 700/90 |
| 2013/0109406 | A1 | 5/2013 | Meador et al. |
| 2014/0022061 | A1 | 1/2014 | Apte et al. |
| 2014/0022793 | A1 | 1/2014 | Apte et al. |
| 2014/0022917 | A1 | 1/2014 | Apte et al. |
| 2014/0022939 | A1 | 1/2014 | Apte et al. |
| 2014/0022940 | A1 | 1/2014 | Apte et al. |
| 2014/0022941 | A1 | 1/2014 | Apte et al. |
| 2014/0022968 | A1 | 1/2014 | Apte et al. |
| 2014/0023060 | A1 | 1/2014 | Apte et al. |
| 2014/0023363 | A1 | 1/2014 | Apte et al. |
| 2014/0025798 | A1 | 1/2014 | Apte et al. |
| 2014/0025805 | A1 | 1/2014 | Apte et al. |

FOREIGN PATENT DOCUMENTS

| | | |
|---|---|---|
| WO | WO 2005/088339 A1 | 9/2005 |
| WO | WO 2006/095315 A1 | 9/2006 |
| WO | WO 2006/095316 A1 | 9/2006 |
| WO | WO 2007/029205 A2 | 3/2007 |
| WO | WO 2008/119158 A1 | 10/2008 |
| WO | WO 2011/087498 A1 | 7/2011 |

OTHER PUBLICATIONS

International Search Report; International Application No. PCT/US2013/050824; date of mailing Jan. 10, 2014; 17 pages.
International Search Report; International Application No. PCT/US2013/050834; date of mailing Dec. 3, 2013; 18 pages.
Invitation to Pay Additional Fees; International Application No. PCT/US2013/050835; date of mailing Oct. 24, 2013; 6 pages.
International Search Report; International Application No. PCT/US2013/050820; date of mailing Oct. 14, 2013; 11 pages.
International Search Report; International Application No. PCT/US2013/050821; date of mailing Jan. 8, 2014; 17 pages.
International Search Report; International Application No. PCT/US2013/050823; date of mailing Oct. 21, 2013; 11 pages.
International Search Report; International Application No. PCT/US2013/050825; date of mailing Oct. 21, 2013; 11 pages.
International Search Report; International Application No. PCT/US2013/050837; date of mailing Jan. 2, 2014; 17 pages.
International Search Report; International Application No. PCT/US2013/050839; date of mailing Jan. 8, 2014; 16 pages.
International Search Report; International Application No. PCT/US2013/050826; date of mailing Dec. 3, 2013; 17 pages.

\* cited by examiner

SYSTEMS AND METHODS FOR WIRELESS CONTROL AND MANAGEMENT

FIELD OF THE INVENTION

The present application relates generally to wireless control and management and specifically to wirelessly controlling devices in an environment.

BACKGROUND OF THE INVENTION

As environments such as homes, offices, retail establishments, etc. become more automated; many of the devices within those environments may be configured for wireless communication. As an example, many homes include a router for facilitating wireless communication with a plurality of devices. While the router may facilitate updates of software on the devices, current solutions do not utilize the wireless functionality to control the devices in the environment. Accordingly, many users within an environment are forced to manually control those devices to set their own lighting, monitor air fresheners, control cleaning devices, order replacement parts, etc.

SUMMARY OF THE INVENTION

Included are embodiments of a method for wireless control and management. More specifically, one embodiment of a system includes a memory component that stores logic that, when executed by the system, causes the system to receive a first signal regarding a device condition of a service device in an environment, determine a condition type of the device condition, and send a first request for to correct the device condition, based on the condition type. In some embodiments, the logic further causes the system to receive a second signal indicating whether the device condition was corrected.

Also included are embodiments of a method. Some embodiments of the method include receiving a first signal from a first service device regarding a detected a device condition of the first service device in an environment, determining a condition type of the device condition, and sending a first request for a second service device to correct the device condition, based on the condition type. Similarly, some embodiments include receiving a second signal from the second service device indicating that the device condition is corrected, sending, by a computing device, a second request to the first service device to determine whether the device condition is corrected, and receiving a response from the first service device regarding whether the device condition is corrected. Still some embodiments include providing an interface indicating whether the device condition is corrected.

Also included are embodiments of a non-transitory computer-readable medium. Some embodiments of the non-transitory computer-readable medium include a program that when executed by a computing device causes the computing device to receive a first signal from a first service device regarding a device condition of the first service device in an environment, determine a condition type of the device condition, and send a first request for a second service device to correct the device condition, based on the condition type. Similarly, in some embodiments the program causes the computing device to receive a second signal from the second service device indicating that the device condition is corrected, send a second request to the first service device to determine whether the device condition is corrected, and receive a response from the first service device regarding whether the device condition is corrected. In still some embodiments, the program causes the computing device to provide an interface indicating whether the device condition is corrected.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

DETAILED DESCRIPTION OF THE INVENTION

Embodiments disclosed herein include systems and methods for wirelessly controlling and managing service devices in an environment. A service device may include any device for performing a service, such as an air freshener, a light source, a cleaning robot, a television, an electronic component, an appliance, a tooth brush, a cleaning supply, pet food, etc. Some embodiments disclosed herein may be configured to utilize a gateway device to control a plurality of different devices in an environment. In some embodiments, the gateway device may be configured to communicate with the service devices using a wired and/or wireless communication protocol. The gateway device may additionally be configured to communicate with other local and/or remote devices. The communication with the other devices may be performed via a wireless router, a wide area wireless protocol and/or a mid-range wireless protocol. Accordingly this gateway device may control the operation and manage the use of the service devices to provide a more fully automated environment, as well as operate the service devices more efficiently. In some embodiments, no gateway device may be necessary, as the service devices may be configured to communicate directly.

Figure 1:
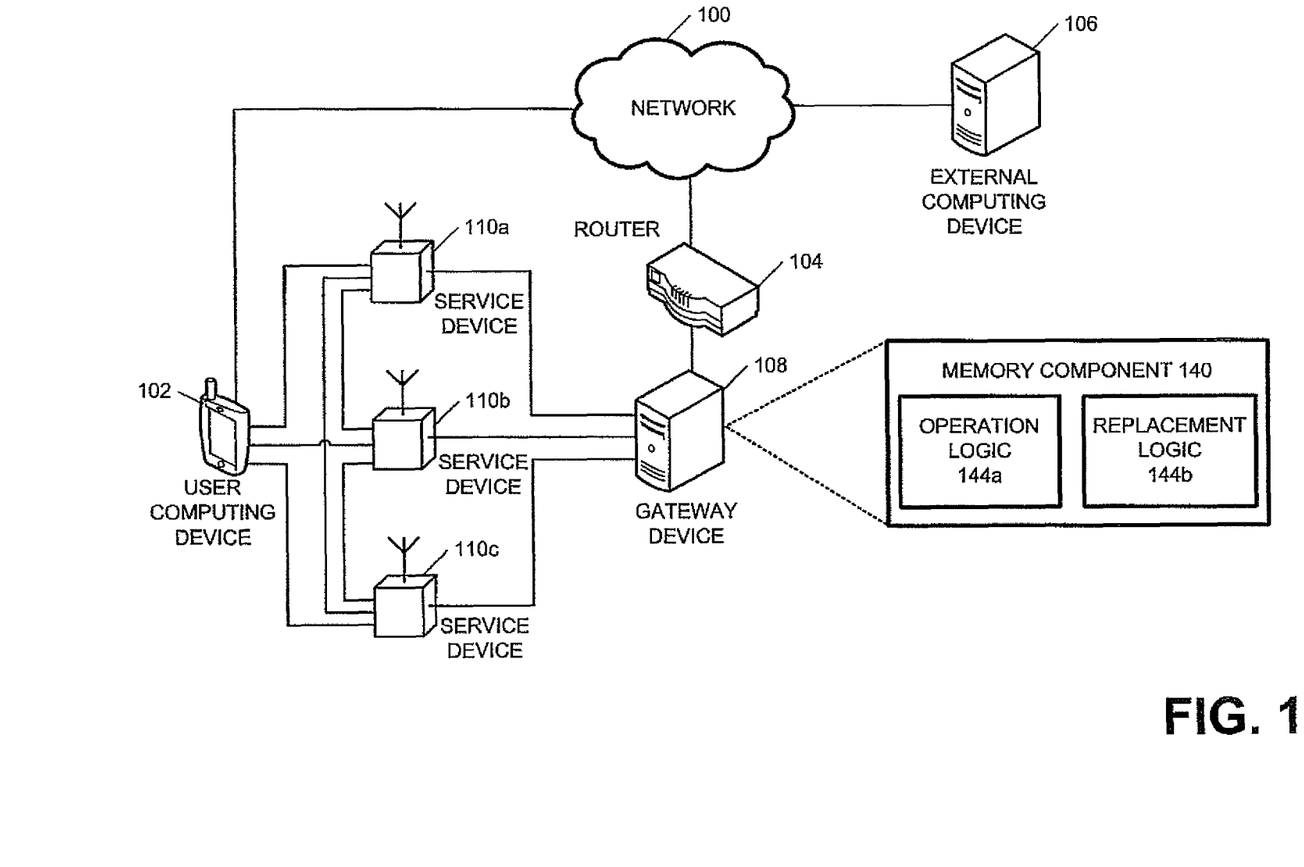
FIG. 1 depicts a computing environment for wireless control and management, according to embodiments disclosed herein.

Referring now to the drawings, FIG. 1 depicts a computing environment for wireless control and management, according to embodiments disclosed herein. As illustrated, a network 100 may be coupled to a user computing device 102, a router 104, and an external computing device 106. The router 104 may be coupled to a gateway device 108, which may be coupled to service devices 110a, 110b, 110c (referred to as "service device 110" to indicate one or more of the service devices 110a, 110b, 110c). The service devices 110 may include any device that is utilized in an environment and may be configured to measure weight, location, temperature, movements, humidity, usage, color, chemical markers, biochemical markers, particles, micro organism, etc. in the environment. In some embodiments this and/or other functionality may be achieved by the service devices 110. As such, the service devices 110 may be configured to monitor/measure aspects of an environment and perform a corresponding action according to the measured environment characteristic. While in some embodiments the corresponding action may be to correct and/or change the environment, in some embodiments, the corresponding action may include communicating with an external computing device to prompt a service call or other action to be performed. Additionally, in some embodiments, the service devices 110 may be configured with wired and/or wireless communication infrastructure (such as Bluetooth™ and/or near field communication capabilities for communicating directly with the user computing device 102 and/or with the other service devices 110. Additionally, the service devices 110 may be configured to communicate utilizing the network 100 utilizing 3G, 4G, WiMax, and/or other wireless or wired wide area communication protocol. Communication between the service devices 110 and the router 104 may be facilitated via a static IP address on one or more of the service devices 110.

As an example, in some embodiments, a first service device 110 (which may be a light fixture) may be configured to determine a device condition, such as identifying the presence of a person in a room. Once the first service device 110 makes this determination, the first service may activate, as well as send a direct signal to a second service device 110 (which may be a television) to activate as well.

The network 100 may include a wide area network and/or a local area network and thus may be wired and/or wireless. The user computing device 102 may include any portable and/or non-portable computing device, such as personal computer, laptop computer, tablet computer, personal digital assistant (PDA), mobile phone, etc. The user computing device 102 may additionally include other communication infrastructure, such as infrared, Wi-Fi™, near field communication, Zigbee, 6lowpan, JennetIP, IPV6 etc. In some embodiments, the user computing device 102 may use one or more of these protocols to function as a remote control of one or more of the service devices 110, as depicted in FIG. 1. Examples of devices and/or software that may be utilized in the embodiment of FIG. 1 may include those produced and/or sold by Energate™, Energyhum™, EnOcean™, Frostdale™, Greenwave™, HAI™, Home Seer™, HomeLogic™, Insteon™, JDS Technologies™, Lagotek™, Levitron™, Lite Touch™, Lutron™, Merten™, PLCBus™, Promixis™, Pulse Worx™, RTI™, Savant™, Schlage™, Stardraw™, Vantage™, Vivint™, X10™, Zensys™, and Zigbee.

The gateway device 108 may be coupled to the router 104 and may include a memory component 140 that stores operation logic 144a and replacement logic 144b. The operation logic 144a may include software, hardware, and/or firmware for providing operational commands to one or more of the service devices 110. Similarly, the replacement logic 144b may include software, hardware, and/or firmware for determining whether the service device 110 is in need of a replacement part, as well as for facilitating the ordering of the replacement part.

Additionally, the external computing device 106 may be configured as a server and/or other computing device for communicating information with the other devices in FIG. 1. In some embodiments, the external computing device 106 may be configured as a web server for placing replacement product orders. Similarly, in some embodiments, the external computing device 106 may be configured to provide a user interface for a user to monitor and/or control the functionality of the service devices 110.

It should be understood that while the user computing device 102, the router 104, the external computing device 106, and the gateway device 108 are represented in FIG. 1 each as a single component; this is merely an example. In some embodiments, there may be numerous different components that provide the described functionality. However, for illustration purposes, single components are shown in FIG. 1 and described herein.

It should also be understood that while FIG. 1 depicts each of the devices 102-110 as being physically coupled to other devices, this is merely an example. More specifically, the embodiment of FIG. 1 is depicted to illustrate a communicative connection between devices. This communicative connection may take the form of a wired connection and/or a wireless connection. Thus, depending on the particular embodiment, a physical connection may or may not actually be implemented. On a similar note, the wireless connection may take any of a number of different forms, including a near field communication protocol (such as Bluetooth™, RF4CE, etc.), a mid-range wireless protocol (such as Wi-Fi™, Wi-Di™, etc.), and/or a long range wireless protocol (such as WiMax, 3G, 4G, etc.).

It should additionally be understood, that while FIG. 1 depicts an example configuration, other configurations are also contemplated and within the scope of this disclosure. More specifically, in some embodiments, the user computing device 102 may act as the gateway device and may be configured to communicate directly with the service device 110. Similarly, in some embodiments, the gateway device 108 may be configured as a router as well and thus may facilitate communication between the user computing device 102 and the service devices 110.

Figure 2:
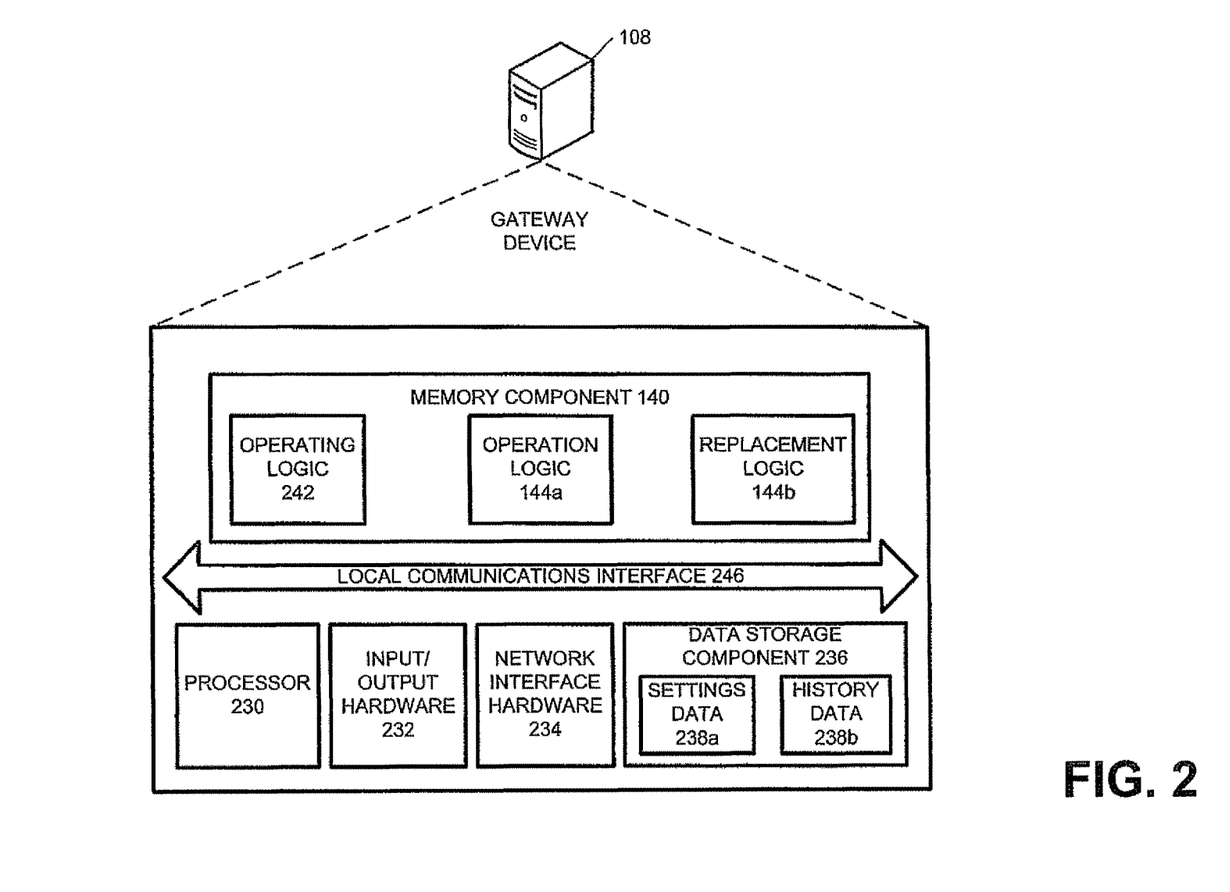
FIG. 2 depicts a gateway device, such as may be used for wireless control and management, according to embodiments disclosed herein.

FIG. 2 depicts a gateway device 108, such as may be used for wireless control and management, according to embodiments disclosed herein. In the illustrated embodiment, the gateway device 108 includes a processor 230, input/output hardware 232, network interface hardware 234, a data storage component 236 (which stores settings data 238a, history data 238b, and/or other data), and the memory component 140. The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, the non-transitory computer-readable medium may reside within the gateway device 108 and/or external to the gateway device 108.

Additionally, the memory component 140 may store operating logic 242, the operation logic 144a, and the replacement logic 144b. The operation logic 144a and the replacement logic 144*b* may each include a plurality of different pieces of logic, each of which may be embodied as a computer program, firmware, and/or hardware, as an example. A local communication interface 246 is also included in FIG. 2 and may be implemented as a bus or other communication interface to facilitate communication among the components of the gateway device 108.

The processor 230 may include any processing component operable to receive and execute instructions (such as from the data storage component 236 and/or the memory component 140). The input/output hardware 232 may include and/or be configured to interface with a monitor, positioning system, keyboard, touch screen, mouse, printer, image capture device, microphone, speaker, gyroscope, compass, and/or other device for receiving, sending, and/or presenting data. The network interface hardware 234 may include and/or be configured for communicating with any wired or wireless networking hardware, including an antenna, a modem, LAN port, wireless fidelity (Wi-Fi) card, Bluetooth™ hardware, WiMax card, mobile communications hardware, and/or other hardware for communicating with other networks and/or devices. From this connection, communication may be facilitated between the gateway device 108 and other computing devices.

The operating logic 242 may include an operating system and/or other software for managing components of the gateway device 108. Similarly, as discussed above, the operation logic 144*a* may reside in the memory component 140 and may be configured to cause the processor 230 to control and/or manage one or more of the service devices 110. Similarly, replacement logic 144*b* may be configured for facilitating the replacement of one or more parts of the service devices 110. Other functionality is also included and described in more detail, below.

It should be understood that the components illustrated in FIG. 2 are merely exemplary and are not intended to limit the scope of this disclosure. While the components in FIG. 2 are illustrated as residing within the gateway device 108, this is merely an example. In some embodiments, one or more of the components may reside external to the gateway device 108. It should also be understood that while the gateway device 108 in FIG. 2 is illustrated as a single device, this is also merely an example. In some embodiments, the operation logic 144*a* and/or the replacement logic 144*b* may reside on different devices. Additionally, while the gateway device 108 is illustrated with the operation logic 144*a* and the replacement logic 144*b* as separate logical components, this is also an example. In some embodiments, a single piece of logic may cause the gateway device 108 to provide the described functionality.

Figure 3:
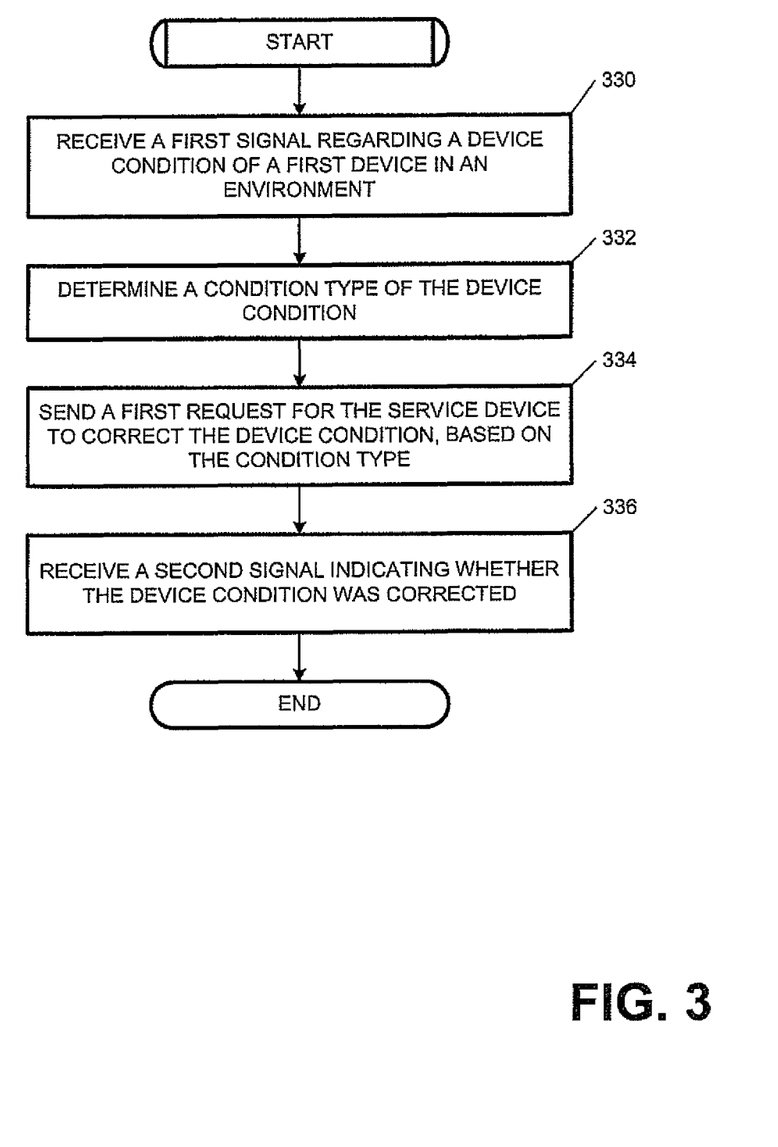
FIG. 3 depicts a flowchart for adjusting a device in an environment, according to embodiments disclosed herein.

FIG. 3 depicts a flowchart for adjusting a device in an environment, according to embodiments disclosed herein. As illustrated in block 330, a first signal regarding a device condition of a first device in an environment may be received. In block 332, a condition type of the device condition may be determined. In block 334, a first request for the service device to correct the device condition may be sent, based on the condition type. In block 336, a second signal indicating whether the device condition was corrected may be received.

Figure 4:
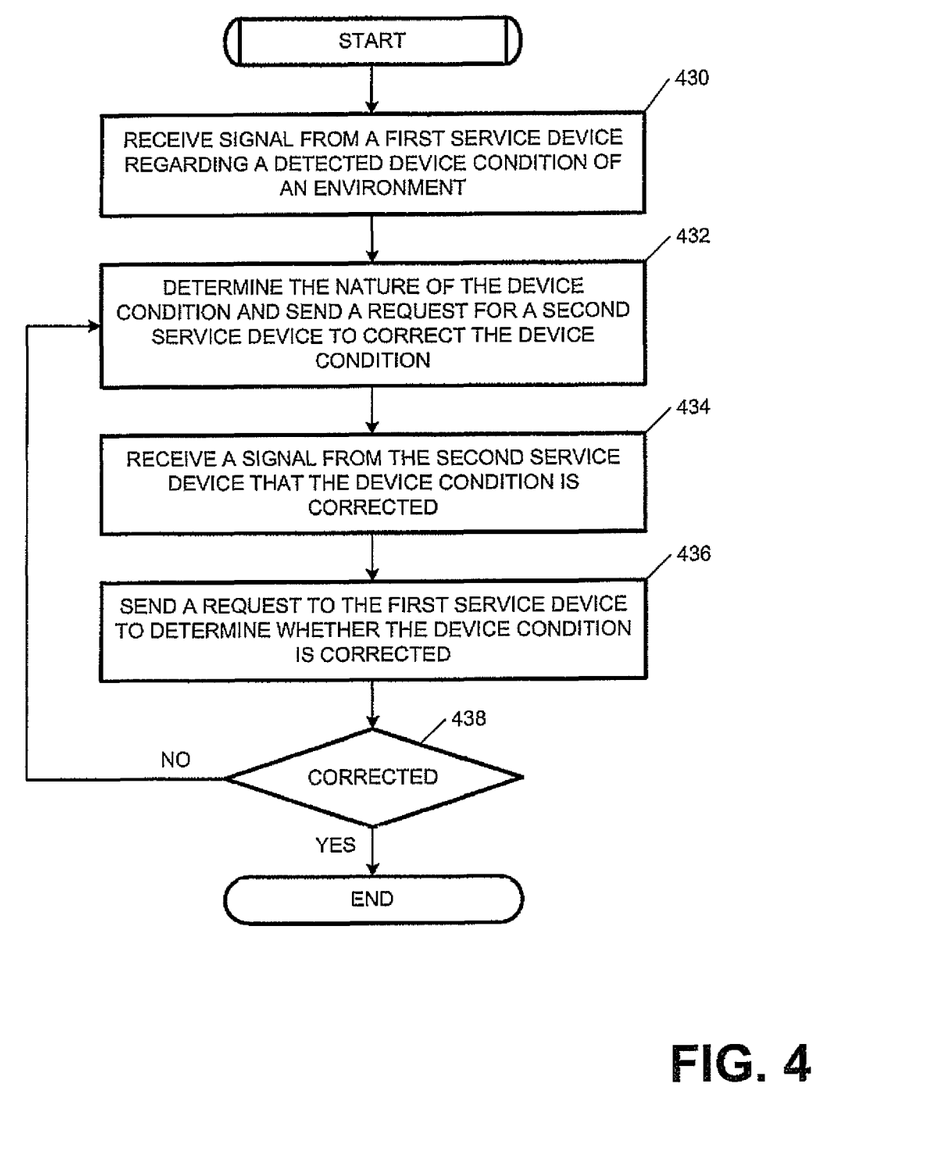
FIG. 4 depicts another flowchart for adjusting a device in an environment, according to embodiments disclosed herein.

FIG. 4 depicts a flowchart for adjusting a device in an environment, according to embodiments disclosed herein. As illustrated in block 430, a signal may be received from a first service device regarding a device condition of the first service device in an environment. A device condition may include any number of condition types, including an odor detected by a service device (and/or type of odor), an absence of perfume ingredients that are dispensed into the air by the service device for predetermined amount of time (and/or type of odor), a lighting intensity of the service device (and/or the degree deficient), a power usage of the service device (and/or the degree deficient), and/or other condition. As an example, the first service device may be an odor sensor that detects a foul odor in a room of a house. After detecting the foul odor, the odor sensor may send a signal to a gateway device. In block 432, a determination may be made regarding the nature of the device condition (e.g., the type of device condition and/or the intensity of the device condition) and a request for a second service device may be sent to correct the device condition.

Continuing with the previous example, the gateway device determines that that device condition is the detection of a foul odor and may additionally determine the type of odor. The gateway device may then send a request to an air freshening device to neutralize the odor. The neutralization may be based on the determined type of odor. In block 434, a signal from the second device may be received indicating that the device condition has been corrected. In block 436, a request may be sent to the first service device to determine whether the device condition has actually been corrected. As the air freshening device may or may not have an odor sensor, the first service device may again be contacted by the gateway device to determine whether the foul odor has been neutralized. In block 438, a response may be received from the first device regarding whether the device condition has been corrected. In block 440 a determination has been made regarding whether the device condition has been corrected. If so, the process may return to block 432. If not, the process may end.

It should be understood that in some embodiments the air freshening device may be configured to dispense a first perfume into the air of an environment and then, to prevent scent habitation, dispense a second scent. As such, the gateway device may determine whether the first scent has been present for a predetermined time and, if so, then send a request to the air freshening device to provide the second scent. Examples of such devices may be provided in U.S. Pat. No. 7,981,367.

Additionally, some embodiments may be configured to create an environment that affects the mood of users in that environment. As an example, a first perfume ingredient may be dispensed into the air of the environment to create a relaxed atmosphere, while a different perfume may be dispensed to create an alert atmosphere. Depending on the time of day, the user, a user selection, the season, and/or other factors, these perfumes may be (independently or collectively) used to create the desired effect.

Similarly, in some embodiments, the number and/or identity of users that enter the environment may also be determined. More specifically, in some embodiments, the service devices and/or gateway device may detect the presence of one or more smart phones, key fobs, etc. Based on the communication with the smart phones, key fobs, etc., a number of users and their identities may be determined. Then, based on the identities and numbers of users, a determination regarding the effects provided to the environment may be made. Examples may be found in U.S. Pat. No. 4,779,198

Further, some embodiments may be configured to sense and clean the air of contaminants, such as volatile organic compounds, malodors, particulates, dust, harmful gasses, viruses, bacteria, pollen, mold, etc. In such embodiments, a determination may be made regarding the type of contaminants present in the environment. Then, the air freshener device may receive an instruction to dispense to appropriate combatant (or otherwise perform an action) to remove that determined contaminant. Examples of such detection and/or treatment may be found in U.S. Patent Publication Number 2008/0182506 and U.S. Patent Publication Number 2009/0293211.

It should also be understood that while the examples provided above relate to an odor detector and air freshener as separate devices, this is merely an example. In some embodiments, the first service device and the second service device may be implemented as a single device. Additionally, while the embodiment described above refers to odor detection and treatment, this is also an example, as any device condition may be detected and/or treated.

Similarly, while the examples provided above relate to the detection of an odor in an environment, other device conditions may additionally be detected and treated. More specifically, in some embodiments, the device condition may be that a toothbrush needs to be replaced. Accordingly, the toothbrush may communicate with the gateway device 108, which may send a signal to the user computing device 102 (and/or the toothbrush) to replace the toothbrush. The user computing device 102 and/or the toothbrush may send a signal back to the gateway device 108 indicating that a new toothbrush has been ordered (and indicate a time for replacement). After the time for replacement, the gateway device 108 may send a signal to determine whether the toothbrush has been replaced. If so, the process may end. If the toothbrush has not been replaced, the gateway device 108 may repeat the process to ensure that the toothbrush is replaced. This process may be utilized to address other device conditions, such as replacement of dog food, laundry detergent, and cleaning supplies, the maintenance of appliances, etc.

Figure 5:
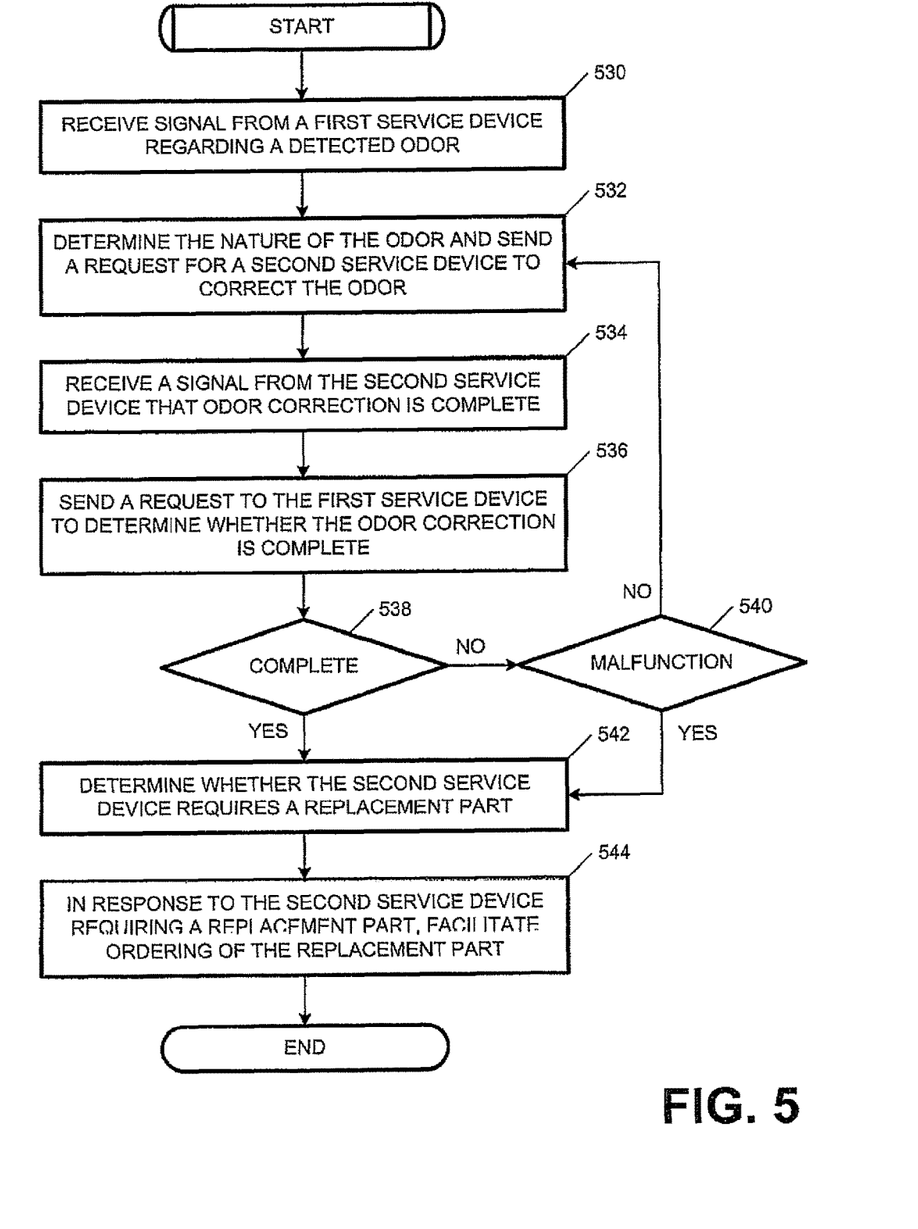
FIG. 5 depicts a flowchart for correcting an odor and ordering replacement parts for a service device, according to embodiments disclosed herein.

FIG. 5 depicts a flowchart for correcting an odor and ordering replacement parts for a device, according to embodiments disclosed herein. As illustrated in block 530, a signal may be received from a first service device regarding a detected odor. In block 532, a determination may be made regarding the nature of the odor and a request may be sent for a second service device to correct the odor. In block 534, a signal may be received from the second service device that the odor correction is complete. In block 536, a request may be sent to the first service device to determine whether the odor correction is complete. In block 538 a determination may be made regarding whether the odor correction is complete. If not, in block 540, a determination may be made regarding whether the second service device is currently experiencing a malfunction. If not, the process may return to 532. If so (or if the odor correction is complete in block 538), in block 542, a determination may be made regarding whether the second service device requires a replacement part (which could be the malfunction). In block 544, in response to a determination that the second service device requires a replacement part, ordering of the replacement part may be facilitated.

Figure 6:
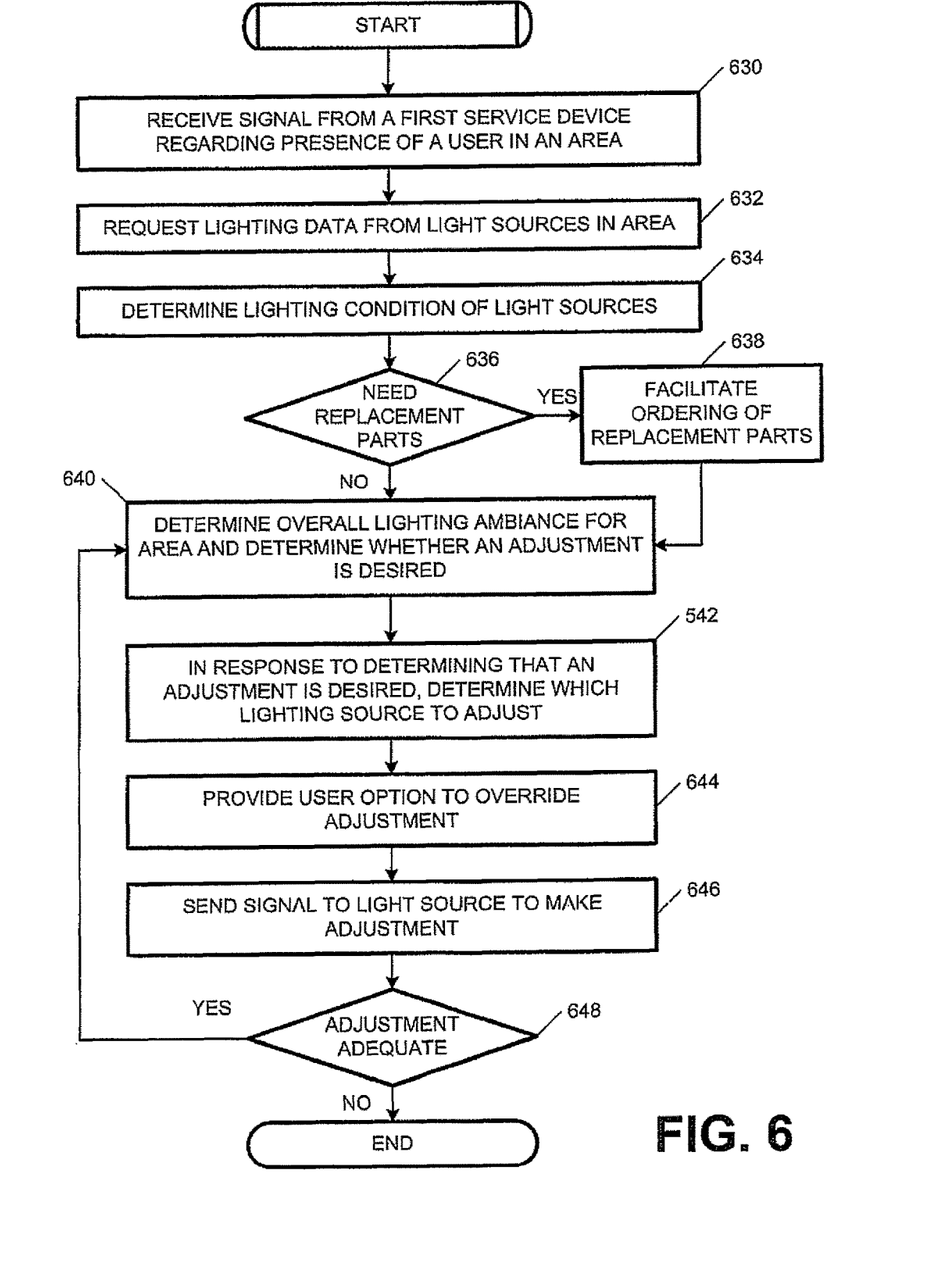
FIG. 6 depicts a flowchart for adjusting the lighting in an environment, according to embodiments disclosed herein.

FIG. 6 depicts a flowchart for adjusting the lighting in an environment, according to embodiments disclosed herein. As illustrated, in block 630, a signal from a first service device may be received regarding presence of a user in an area of an environment. In block 632, lighting data may be requested from light sources in the area. In block 634, the lighting condition of the light sources may be determined. In block 636, determination may be made regarding whether the light sources need replacement parts. If so in block 638, ordering of the replacement parts may be facilitated. If not (and/or after replacement parts have been ordered), in block 640, an overall lighting ambience may be determined for the area, as well as whether an adjustment is desired. In block 642, in response to determining that an adjustment is desired, a determination may be made regarding which light source to adjust. In block 644, an option may be provided to a user for overriding the adjustment. More specifically, the user may wish to not make the adjustment and may provide this indication to the system. In block 646, a signal may be sent to the light source to make the adjustment. In block 646, a determination may be made regarding whether the adjustment is adequate. If not, the process may return to block 640. If the adjustment is adequate, the process may end.

Additionally, it should be understood that some embodiments may automatically determine when to activate various features. More specifically, if an embodiment determines that a user returns to an environment every Monday-Friday around 5:30 PM, a signal may be sent to automatically change lighting, air fresheners, air quality, etc. to match the preferences for that user at those times. Similarly, if the user prefers a predetermined scent, sound, and/or lighting to sleep or wake, these environmental preferences may be implemented based on those preferences, and at the times that the user sleeps and wakes. See U.S. Pat. No. 7,016,933 for examples.

Figure 7:
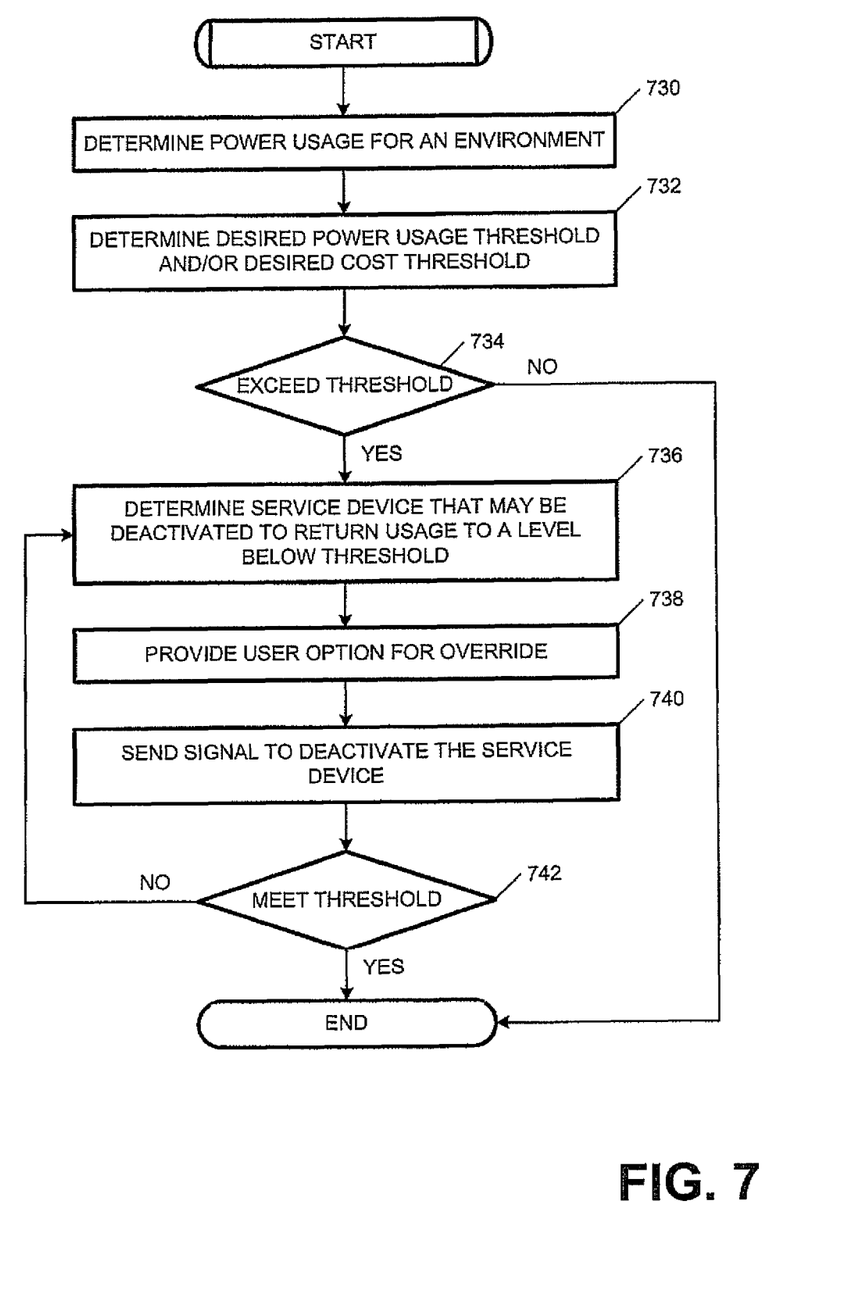
FIG. 7 depicts a flowchart for controlling power usage of devices in an environment, according to embodiments disclosed herein.

FIG. 7 depicts a flowchart for controlling power usage of devices in an environment, according to embodiments disclosed herein. As illustrated in block 730, a power usage may be determined for an environment. In block 732, a desired power usage threshold and/or a desired cost threshold may be determined. In block 734, a determination may be made regarding whether the environment is currently exceeding the determined threshold. If not, the process may end. If the threshold is currently being exceeded, in block 736 a determination may be made regarding a service device that may be deactivated (or otherwise altered) to return the usage to a level below the threshold. In block 738, a user option may be provided for a user to override deactivation. In block 740, a signal may be sent to deactivate the determined device. In block 742, a determination may be made regarding whether the environment now meets (or is below) the threshold. If not, the process returns to block 736. If the threshold is meeting (or is below) the threshold, the process may end.

Figure 8:
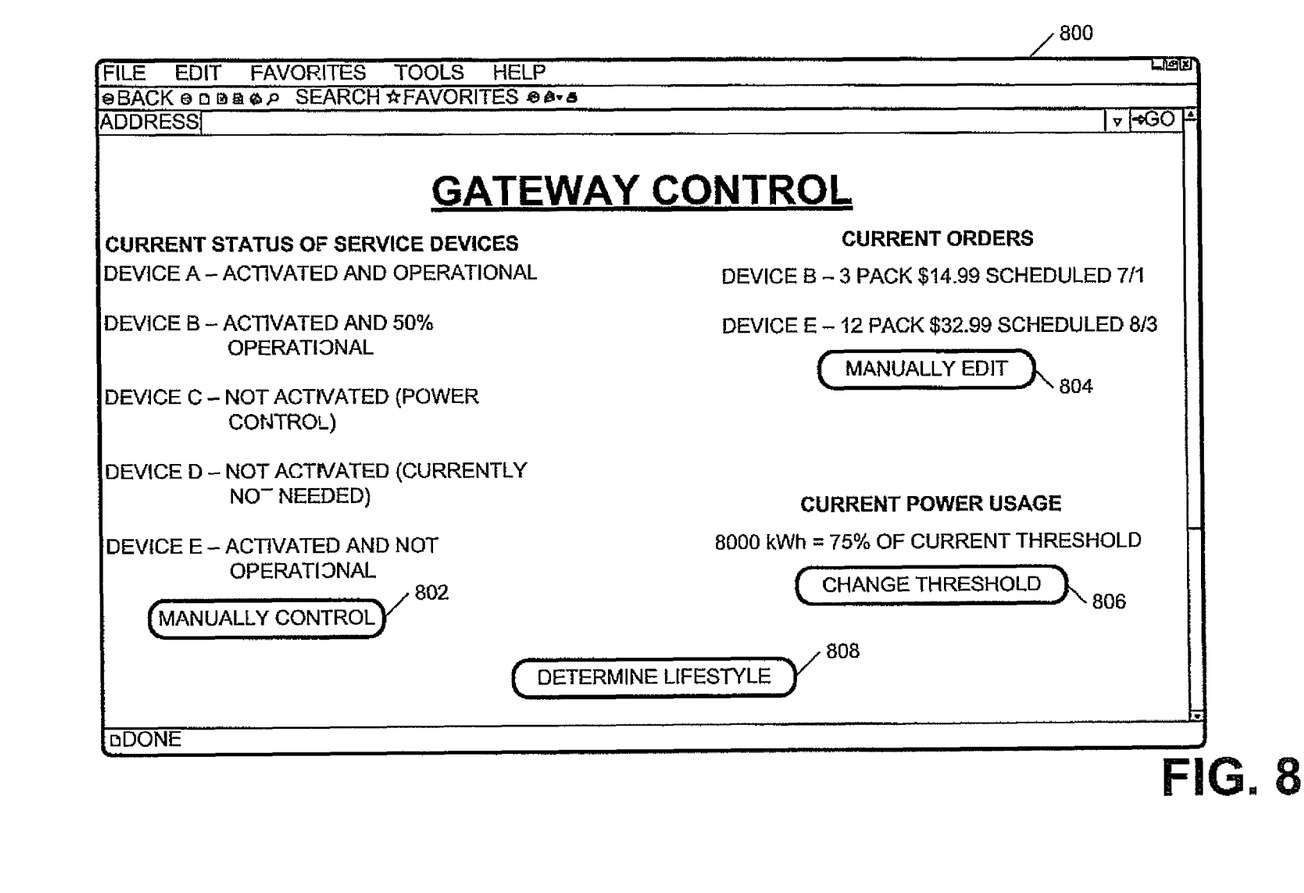
FIG. 8 depicts an interface for wirelessly controlling and managing service devices in an environment, according to embodiments disclosed herein.

FIG. 8 depicts an interface 800 for wirelessly controlling and managing devices in an environment, according to embodiments disclosed herein. Depending on the particular embodiment, the interface 800 may be provided by the user computing device 102 with data received from the gateway device 108 and/or from the external computing device 106. Regardless, the interface 800 includes a listing of the current status of one or more of the service devices 110. Additionally included is a manual option 802 to manually control functionality of the service devices 110. Also included is a listing of current orders for replacement parts, as well as an edit option 804 to edit the parameters of the orders. A current power usage may also be provided with a threshold option 806 to manually change a power and/or cost threshold.

Also included is a determine lifestyle option 808. By selecting the lifestyle option 808, the user may be provided with one or more questions for determining a lifestyle of the user. Once the questions are answered, a theme may be determined to be implemented for the user.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be understood to those skilled in the art that various other changes and modifications can be made without departing from the spirit and scope of the invention. It is therefore intended to cover in the appended claims all such changes and modifications that are within the scope of this invention.

What is claimed is:

1. A system for wireless control and management of a lighting system comprising:
    a memory component that stores logic that when executed by the system and causes the system to perform at least the following:
    a) receive a first signal regarding the presence of a user in a first environment;
    b) request lighting data from at least one light source located in the first environment;
    c) determine a condition of the light source;
    d) determine a first overall lighting ambiance for the first environment;
    e) determine whether an adjustment is to be made based on predetermined parameters;
    f) determine which light source to adjust if an adjustment is to be made;
    g) provide a signal to the user to indicate the adjustment that is to be made;
    h) provide the user with an option to override the adjustment;
    i) if the user does not override the adjustment, send a first request to make the adjustment;
    j) determine a second overall ambiance of the environment; and
    k) determine if the second overall ambiance is adequate based on the predetermined parameters, wherein steps d-k are repeated until the second overall ambiance is adequate.

2. The system of claim 1, wherein, in response to a determination that the second ambiance is not adequate, the logic further causes the system to determine whether there is a malfunction with the lighting system.

3. The system of claim 1, wherein the logic further causes the system to determine whether the lighting system requires a replacement part.

4. The system of claim 3, wherein, in response to a determination that the lighting system requires the replacement part, the logic further causes the system to facilitate ordering the replacement part.

5. The system of claim 1, further comprising a gateway device for wirelessly communicating with the lighting system.

6. A non-transitory computer-readable medium for wireless control and management that stores a program that causes a computing device to perform at least the following:
    receive a first signal from a first service device regarding a device condition of the first service device in an environment;
    determine a first condition of the first service device;
    send a first request for a second service device to correct the first condition of the first service device;
    receive a second signal from the second service device indicating that the first condition is corrected;
    send a second request to the first service device to determine whether the first condition is corrected;
    receive a response from the first service device regarding whether the first condition is corrected;
    provide an interface indicating whether the first condition is corrected;
    if the first condition is not corrected, determine whether there is a malfunction in the first service device; and
    provide an interface indicating whether there is a malfunction in the first service device.

* * * * *